(12) United States Patent
Tanner et al.

(10) Patent No.: US 10,213,264 B2
(45) Date of Patent: Feb. 26, 2019

(54) CATHETER TENSION SENSING

(71) Applicant: Hansen Medical, Inc., Mountain View, CA (US)

(72) Inventors: Neal A. Tanner, Burnet, TX (US); Matthew J. Roelle, Sunnyvale, CA (US); Gregory J. Stahler, Belmont, CA (US); Robert G. Younge, Portola Valley, CA (US); Travis Covington, Sunnyvale, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/357,537

(22) Filed: Nov. 21, 2016

(65) Prior Publication Data

US 2017/0119484 A1 May 4, 2017

Related U.S. Application Data

(63) Continuation of application No. 14/214,711, filed on Mar. 15, 2014, now Pat. No. 9,498,601, which is a continuation-in-part of application No. 13/828,342, filed on Mar. 14, 2013, now Pat. No. 9,173,713.

(60) Provisional application No. 61/793,347, filed on Mar. 15, 2013.

(51) Int. Cl.
*A61F 2/95* (2013.01)
*A61M 25/01* (2006.01)
*A61B 34/00* (2016.01)
*A61B 17/00* (2006.01)
(Continued)

(52) U.S. Cl.
CPC .............. *A61B 34/71* (2016.02); *A61B 34/30* (2016.02); *A61B 90/06* (2016.02); *A61M 25/0147* (2013.01); *A61B 2017/00477* (2013.01); *A61B 2034/301* (2016.02); *A61B 2034/715* (2016.02);
(Continued)

(58) Field of Classification Search
CPC ... A61B 1/00; A61B 1/00048; A61B 1/00149; A61B 1/00188; A61B 34/71; A61B 34/00; A61B 34/30; A61F 2/95; A61F 2/958; A61F 2017/1205; A61M 25/00; A61M 25/01; A61M 25/0147
See application file for complete search history.

(56) References Cited

U.S. PATENT DOCUMENTS

| 2,556,601 A | 6/1951 | Schofield |
| 2,566,183 A | 8/1951 | Forss |
| 2,730,699 A | 1/1956 | Gratian |

(Continued)

FOREIGN PATENT DOCUMENTS

| CN | 101500470 | 8/2009 |
| CN | 102665590 | 9/2012 |

(Continued)

OTHER PUBLICATIONS

Search Report for European Patent Application No. 14160090.8 dated Feb. 5, 2015. (6 pages).

(Continued)

*Primary Examiner* — Victor Nguyen
(74) *Attorney, Agent, or Firm* — Knobbe, Martens, Olson & Bear, LLP

(57) ABSTRACT

This disclosure covers various concepts to use for obtaining measurement of tension in catheter pullwires to improve controllability of a robotic surgical system.

20 Claims, 14 Drawing Sheets

(51) Int. Cl.
*A61B 34/30* (2016.01)
*A61B 90/00* (2016.01)

(52) U.S. Cl.
CPC .. *A61B 2090/066* (2016.02); *A61M 2025/015* (2013.01); *A61M 2025/0166* (2013.01)

(56) References Cited

U.S. PATENT DOCUMENTS

| | | |
|---|---|---|
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,398,691 A | 3/1995 | Martin et al. |
| 5,408,409 A | 4/1995 | Glassman et al. |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,631,973 A | 5/1997 | Green |
| 5,713,946 A | 2/1998 | Ben-Haim |
| 5,749,362 A | 5/1998 | Funda et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,859,934 A | 1/1999 | Green |
| 5,876,325 A | 3/1999 | Mizuno et al. |
| 5,921,968 A | 7/1999 | Lampropoulos et al. |
| 5,951,475 A | 9/1999 | Gueziec et al. |
| 5,967,934 A | 10/1999 | Ishida et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,226,543 B1 | 5/2001 | Gilboa et al. |
| 6,259,306 B1 | 7/2001 | Green |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,424,885 B1 | 7/2002 | Niemeyer et al. |
| 6,436,107 B1 * | 8/2002 | Wang ............. A61B 1/00149 318/568.11 |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,155,315 B2 | 12/2006 | Niemeyer et al. |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,618,371 B2 | 11/2009 | Younge et al. |
| 7,635,342 B2 | 12/2009 | Ferry et al. |
| 7,766,856 B2 | 8/2010 | Ferry et al. |
| 7,850,642 B2 | 12/2010 | Moll et al. |
| 7,935,059 B2 | 5/2011 | Younge et al. |
| 7,938,809 B2 | 5/2011 | Lampropoulos et al. |
| 7,972,298 B2 | 7/2011 | Wallace et al. |
| 7,974,674 B2 | 7/2011 | Hauck et al. |
| 7,974,681 B2 | 7/2011 | Wallace et al. |
| 7,976,539 B2 | 7/2011 | Hlavka et al. |
| 7,998,020 B2 | 8/2011 | Kidd et al. |
| 8,021,326 B2 | 9/2011 | Moll et al. |
| 8,041,413 B2 | 10/2011 | Barbagli et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,108,069 B2 | 1/2012 | Stahler et al. |
| 8,157,308 B2 | 4/2012 | Pedersen |
| 8,182,415 B2 | 5/2012 | Larkin et al. |
| 8,257,303 B2 | 9/2012 | Moll et al. |
| 8,285,364 B2 | 10/2012 | Barbagli et al. |
| 8,290,571 B2 | 10/2012 | Younge et al. |
| 8,291,791 B2 | 10/2012 | Light et al. |
| 8,317,746 B2 | 11/2012 | Sewell et al. |
| 8,388,538 B2 | 3/2013 | Younge et al. |
| 8,388,556 B2 | 3/2013 | Wallace et al. |
| 8,394,054 B2 | 3/2013 | Wallace et al. |
| 8,409,136 B2 | 4/2013 | Wallace et al. |
| 8,409,172 B2 | 4/2013 | Moll et al. |
| 8,409,234 B2 | 4/2013 | Stahler et al. |
| 8,460,236 B2 | 6/2013 | Roelle et al. |
| 8,515,215 B2 | 8/2013 | Younge et al. |
| 8,617,102 B2 | 12/2013 | Moll et al. |
| 8,657,781 B2 | 2/2014 | Sewell et al. |
| 8,672,837 B2 | 3/2014 | Roelle et al. |
| 8,705,903 B2 | 4/2014 | Younge et al. |
| 8,720,448 B2 | 5/2014 | Reis et al. |
| 8,746,252 B2 | 6/2014 | McGrogan et al. |
| 8,801,661 B2 | 8/2014 | Moll et al. |
| 8,811,777 B2 | 8/2014 | Younge et al. |
| 8,818,143 B2 | 8/2014 | Younge et al. |
| 8,864,655 B2 | 10/2014 | Ramamurthy et al. |
| 8,926,603 B2 | 1/2015 | Hlavka et al. |
| 8,961,533 B2 | 2/2015 | Stahler et al. |
| 8,974,408 B2 | 3/2015 | Wallace et al. |
| 9,014,851 B2 | 4/2015 | Wong et al. |
| 9,057,600 B2 | 6/2015 | Walker et al. |
| 9,138,166 B2 | 9/2015 | Wong et al. |
| 9,173,713 B2 | 11/2015 | Hart et al. |
| 9,186,046 B2 | 11/2015 | Ramamurthy et al. |
| 9,186,047 B2 | 11/2015 | Ramamurthy et al. |
| 9,204,933 B2 | 12/2015 | Reis et al. |
| 9,254,123 B2 | 2/2016 | Alvarez et al. |
| 9,271,663 B2 | 3/2016 | Walker et al. |
| 9,289,578 B2 | 3/2016 | Walker et al. |
| 9,326,822 B2 | 5/2016 | Lewis et al. |
| 9,404,734 B2 | 8/2016 | Ramamurthy et al. |
| 9,408,669 B2 | 8/2016 | Kokish et al. |
| 9,441,954 B2 | 9/2016 | Ramamurthy et al. |
| 9,452,018 B2 | 9/2016 | Yu |
| 9,457,168 B2 | 10/2016 | Moll et al. |
| 9,498,601 B2 | 11/2016 | Tanner et al. |
| 9,500,472 B2 | 11/2016 | Ramamurthy et al. |
| 9,500,473 B2 | 11/2016 | Ramamurthy et al. |
| 9,504,604 B2 | 11/2016 | Alvarez |
| 9,561,083 B2 | 2/2017 | Yu et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,636,483 B2 | 5/2017 | Hart et al. |
| 9,668,814 B2 | 6/2017 | Kokish |
| 9,710,921 B2 | 7/2017 | Wong et al. |
| 9,713,509 B2 | 7/2017 | Schuh et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |

(56) References Cited

U.S. PATENT DOCUMENTS

| | | |
|---|---|---|
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,931,025 B1 | 4/2018 | Graetzel et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0117017 A1 | 8/2002 | Bernhardt et al. |
| 2002/0161355 A1 | 10/2002 | Wollschlager |
| 2002/0177789 A1 | 11/2002 | Ferry et al. |
| 2004/0015053 A1 | 1/2004 | Bieger |
| 2004/0152972 A1 | 8/2004 | Hunter |
| 2004/0243147 A1 | 12/2004 | Lipow |
| 2005/0183532 A1 | 8/2005 | Najaf et al. |
| 2005/0222554 A1 | 10/2005 | Wallace et al. |
| 2006/0025676 A1 | 2/2006 | Viswanathan et al. |
| 2006/0111692 A1 | 5/2006 | Hlavka et al. |
| 2006/0200026 A1 | 9/2006 | Wallace et al. |
| 2006/0201688 A1 | 9/2006 | Jenner et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0112355 A1 | 5/2007 | Salahieh |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0027464 A1 | 1/2008 | Moll et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0262480 A1 | 10/2008 | Stahler et al. |
| 2008/0262513 A1 | 10/2008 | Stahler et al. |
| 2008/0302200 A1 | 12/2008 | Tobey |
| 2009/0024141 A1 | 1/2009 | Stahler et al. |
| 2009/0076476 A1 | 3/2009 | Barbagli et al. |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0138025 A1 | 5/2009 | Stahler et al. |
| 2009/0228020 A1 | 9/2009 | Wallace et al. |
| 2009/0247944 A1 | 10/2009 | Kirschenman et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0125284 A1 | 5/2010 | Tanner et al. |
| 2010/0130987 A1 | 5/2010 | Wenderow et al. |
| 2010/0204646 A1 | 8/2010 | Plicchi et al. |
| 2010/0210923 A1* | 8/2010 | Li .................. A61B 5/042 600/301 |
| 2010/0228191 A1 | 9/2010 | Alvarez et al. |
| 2010/0248177 A1 | 9/2010 | Mangelberger et al. |
| 2010/0280525 A1 | 11/2010 | Alvarez et al. |
| 2010/0331856 A1 | 12/2010 | Carlson et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0238083 A1 | 9/2011 | Moll et al. |
| 2011/0261183 A1 | 10/2011 | Ma et al. |
| 2011/0270273 A1 | 11/2011 | Moll et al. |
| 2011/0277775 A1 | 11/2011 | Holop et al. |
| 2011/0288573 A1 | 11/2011 | Yates et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0306836 A1 | 12/2011 | Ohline et al. |
| 2011/0319910 A1 | 12/2011 | Roelle et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0116253 A1 | 5/2012 | Wallace et al. |
| 2012/0123441 A1 | 5/2012 | Au et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0239012 A1 | 9/2012 | Laurent et al. |
| 2012/0283747 A1 | 11/2012 | Popovic |
| 2012/0296161 A1 | 11/2012 | Wallace et al. |
| 2013/0018400 A1 | 1/2013 | Milton et al. |
| 2013/0030363 A1 | 1/2013 | Wong et al. |
| 2013/0072787 A1 | 3/2013 | Wallace et al. |
| 2013/0085330 A1 | 4/2013 | Ramamurthy et al. |
| 2013/0085331 A1 | 4/2013 | Ramamurthy et al. |
| 2013/0085333 A1 | 4/2013 | Ramamurthy et al. |
| 2013/0090528 A1 | 4/2013 | Ramamurthy et al. |
| 2013/0090530 A1 | 4/2013 | Ramamurthy |
| 2013/0090552 A1 | 4/2013 | Ramamurthy et al. |
| 2013/0144116 A1 | 6/2013 | Cooper et al. |
| 2013/0165945 A9 | 6/2013 | Roelle |
| 2013/0190741 A1 | 7/2013 | Moll et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0222019 A1 | 8/2014 | Brudnick |
| 2014/0264081 A1 | 9/2014 | Walker et al. |
| 2014/0275988 A1 | 9/2014 | Walker et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276933 A1 | 9/2014 | Hart et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0277334 A1 | 9/2014 | Yu et al. |
| 2014/0309649 A1 | 10/2014 | Alvarez et al. |
| 2014/0357953 A1 | 12/2014 | Roelle et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0001038 A1 | 1/2016 | Romo et al. |
| 2016/0007881 A1 | 1/2016 | Wong et al. |
| 2016/0067009 A1 | 3/2016 | Ramamurthy et al. |
| 2016/0166234 A1 | 6/2016 | Zhang et al. |
| 2016/0202053 A1 | 7/2016 | Walker et al. |
| 2016/0228032 A1 | 8/2016 | Walker et al. |
| 2016/0235946 A1 | 8/2016 | Lewis et al. |
| 2016/0270865 A1 | 9/2016 | Landey et al. |
| 2016/0287279 A1 | 10/2016 | Bovay et al. |

(56) References Cited

U.S. PATENT DOCUMENTS

| | | |
|---|---|---|
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0065364 A1 | 3/2017 | Schuh et al. |
| 2017/0065365 A1 | 3/2017 | Schuh |
| 2017/0071684 A1 | 3/2017 | Kokish et al. |
| 2017/0086929 A1 | 3/2017 | Moll et al. |
| 2017/0100084 A1 | 4/2017 | Walker et al. |
| 2017/0100199 A1 | 4/2017 | Yu et al. |
| 2017/0105804 A1 | 4/2017 | Yu |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0215978 A1 | 8/2017 | Wallace et al. |
| 2017/0252540 A1 | 9/2017 | Weitzner et al. |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0055583 A1 | 3/2018 | Schuh et al. |
| 2018/0056044 A1 | 3/2018 | Choi |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 3 025 630 | 6/2016 |
| JP | 2009-139187 | 6/2009 |
| JP | 2010-046384 | 3/2010 |
| WO | WO 02/074178 | 9/2002 |
| WO | WO 03/086190 A1 | 10/2003 |
| WO | WO 09/092059 | 7/2009 |
| WO | WO 11/005335 | 1/2011 |
| WO | WO 13/179600 | 12/2013 |
| WO | WO 15/127231 | 8/2015 |

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

* cited by examiner

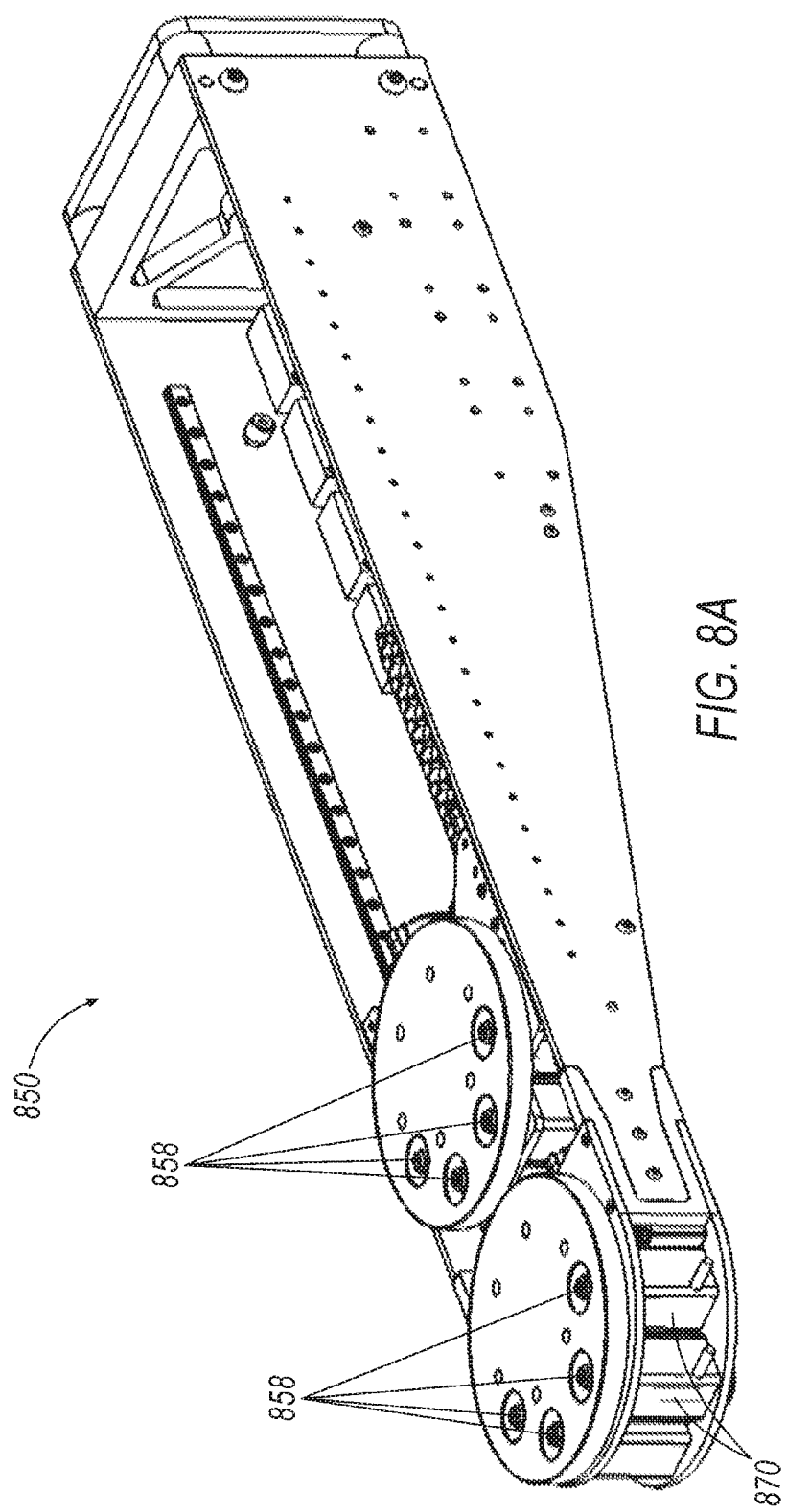

CATHETER TENSION SENSING

CROSS REFERENCE TO RELATED APPLICATIONS

This application is a continuation of U.S. patent application Ser. No. 14/214,711 filed Mar. 15, 2014 entitled "CATHETER TENSION SENSING," which is a continuation-in-part application of U.S. patent application Ser. No. 13/828,342 filed Mar. 14, 2013, and also claims priority to U.S. Provisional Patent Application No. 61/793,347 filed Mar. 15, 2013. The contents of each of the above applications are hereby incorporated by reference in their entirety for all purposes.

TECHNICAL FIELD

The present disclosure generally relates to robotic surgical system for performing minimally invasive diagnostic and therapeutic procedures and particularly to how to measure tension in catheter pullwires in a robotic catheter systems for steerable catheters.

BACKGROUND

Robotic surgical systems and devices are well suited for use in performing minimally invasive medical procedures, as opposed to conventional techniques that may require large incisions to open the patient's body cavity to provide the surgeon with access to internal organs. For example, a robotic surgical system may be utilized to facilitate imaging, diagnosis, and treatment of tissues which may lie deep within a patient, and which may be preferably accessed only via naturally-occurring pathways such as blood vessels or the gastrointestinal tract.

One such robotic surgical system that may be utilized in a minimally invasive procedure is a robotic catheter system. A robotic catheter system utilizes a robot, external to the patient's body cavity, to insert a catheter through a small incision in a patient's body cavity and guide the catheter to a location of interest. Catheters may be steerable for movement in multiple axes including axial insertion/retraction, axial rotation, and deflection/articulation, which encompasses radial bending in multiple directions. To accomplish steering, one or more pullwires are attached to the distal end of an articulating section of a catheter and extend the length of the catheter. The distal tip of a catheter may then be controlled via the pullwires, i.e., by selectively operating tensioning control elements within the catheter instrument.

Kinematic modeling is utilized to predict catheter tip movement within the patient anatomy. The amount of displacement of a pullwire is generally proportional to the amount of articulation. However, at times the calculated motion of the catheter does not precisely match the actual motion within the patient's anatomy. Various elements can affect the amount of articulation for a given pullwire actuation, including the presence of unanticipated or un-modeled constraints imposed by the patient's anatomy, particularly given the tortuous path that the catheter must traverse. Minimization of differences between actual and predicted kinematic functions is desirable to achieve a highly controllable robotic surgical system.

In known robotic catheter systems, shafts that actuate the pullwires are connected through transmission elements to motors. Each motor is equipped with an encoder. However, the load transmitted to an output shaft, as well as the position of the output shaft, is not known. Additionally, while the position of the output shaft is calculated, the torque applied at the output shaft cannot be precisely calculated because of the variations in transmission efficiency and the effects of perturbations on the system due to catheter construction shape and use. Moreover, external forces on the catheter can change the loading on the catheter pullwires and, for a fixed position of the output shaft, in turn may change the torsion loading on the output shafts.

Accordingly, there is a need for a robotic catheter system and method of using the same that addresses the above problems.

SUMMARY

Exemplary illustrations are provided herein of a robotic surgical system, which may include a control system configured to be connected to an input device and to receive information for positioning or orienting a catheter from the input device. The system may further include at least one instrument driver operatively connected to the control system. An exemplary instrument driver may include at least one rotary output motor configured to actuate movement of an elongate member. The control system is configured to actuate the at least one output motor in response to the information to drive an output shaft in communication with the elongate member, and the instrument driver is configured to determine an output shaft torque imparted by the output shaft to the elongate member.

An exemplary method of measuring an output torque may include providing a rotary output shaft configured to actuate an elongate member, and at least one output motor configured to actuate movement of the elongate member by driving the output shaft. The exemplary method may further include determining an output torque of the output shaft based at least upon a sensor input.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

FIG. 8A is a perspective view of an exemplary instrument driver for a catheter assembly, which employs rotary torque sensors.

DETAILED DESCRIPTION

Figure 1:
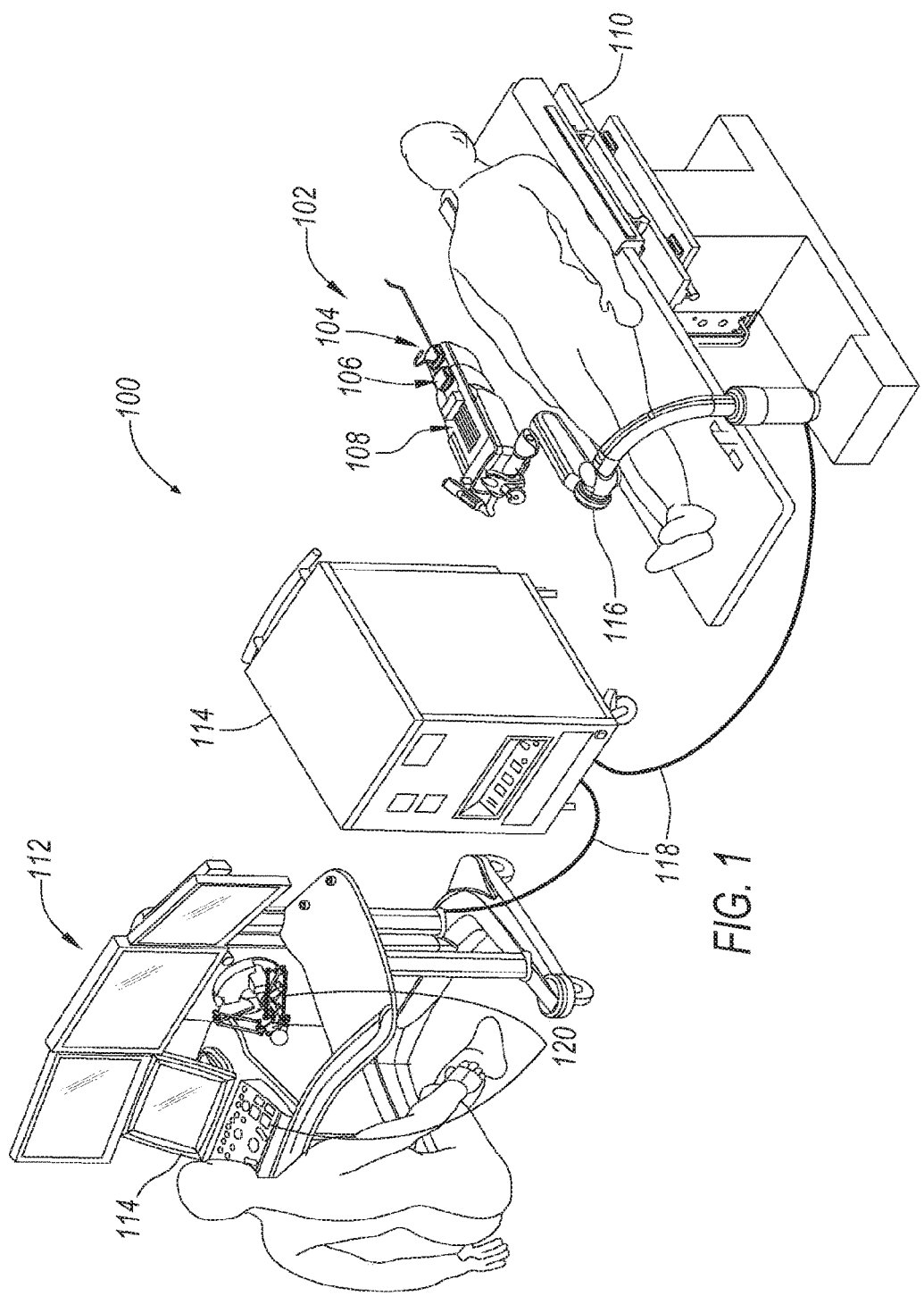
FIG. 1 illustrates an exemplary robotic surgical system.

Referring now to the discussion that follows and also to the drawings, illustrative approaches to the disclosed assemblies are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Referring to FIG. 1, a robotic surgical system 100 is illustrated in which an apparatus, a system, and/or method may be implemented according to various exemplary illustrations. System 100 may include a robotic catheter assembly 102 having a sheath instrument 104 and/or a catheter instrument 106. Catheter assembly 102 is controllable using a robotic instrument driver 108 (generally referred to as "instrument driver"). During use, a patient is positioned on an operating table or surgical bed 110 to which robotic instrument driver 108 is coupled or mounted. In the illustrated example, system 100 includes an operator workstation 112, an electronics rack 114 including a control computer (not shown), a setup joint mounting brace 116, and instrument driver 108. A surgeon is seated at operator workstation 112 and can monitor the surgical procedure, patient vitals, and control one or more catheter devices.

Operator workstation 112 may include a computer monitor to display a three dimensional object, such as a catheter displayed within or relative to a three dimensional space, such as a body cavity or organ, e.g., a chamber of a patient's heart. In one example, an operator uses one or more input devices 120 to control the position of a catheter or other elongate instrument. In response to actuation of the input device by a user, the input device can output information for the desired position or orientation of the catheter instrument, including the three-dimensional spatial position and/or orientation of the distal end of a steerable catheter. System components, including the operator workstation, electronics rack and the instrument driver, may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while located away from or remotely from radiation sources. Because of the option for wireless or networked operation, the surgeon may even be located remotely from the patient in a different room or building.

Figure 2:
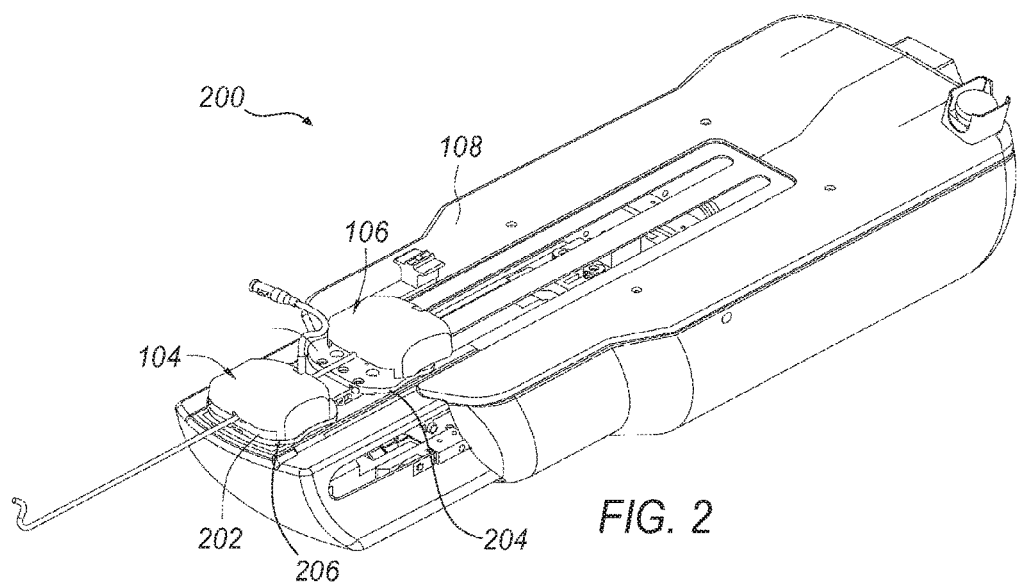
FIG. 2 is an illustration of an exemplary catheter assembly of the surgical system of FIG. 1.

Referring now to FIG. 2, motors within instrument driver 108 are controlled such that carriages coupled to mounting plates 204, 206 are driven forwards and backwards on bearings. As a result, a catheter can be controllably manipulated while inserted into the patient or retracted out of the patient. Instrument driver 108 contains motors that may be activated to control bending of the catheter as well as the orientation of the distal tips thereof, including tools mounted at the distal tip.

Figure 3:
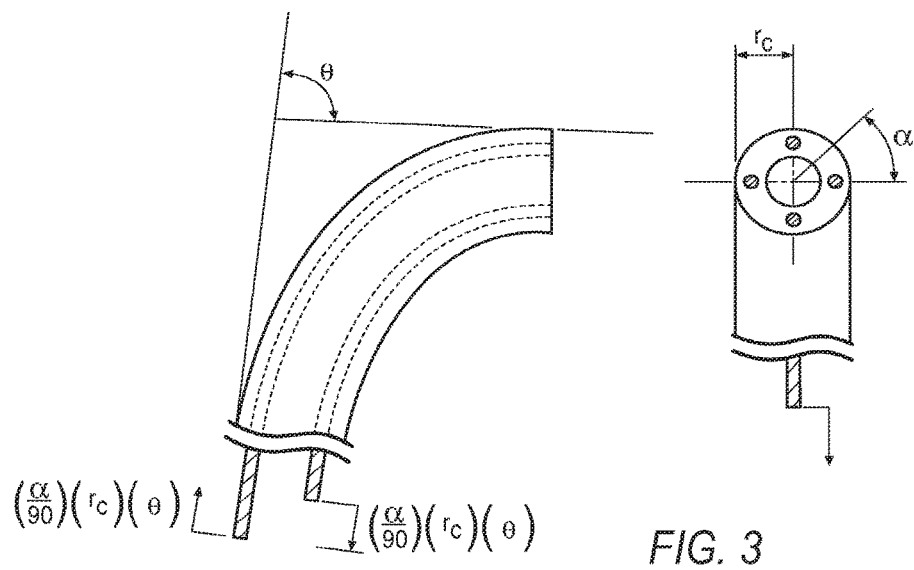
FIG. 3 is a schematic showing a kinematic relationship between pullwire displacement and catheter tip articulation.

The articulation of catheters is normally performed by actuating pullwires that extend the length of the catheter and are attached to the distal end of an articulating section of a catheter. In order to articulate the catheter, the pullwire is displaced at the proximal end to articulate the distal end of the catheter. Typically, the amount that an articulating section of a catheter articulates is determined by calculating the change in path length that an actuating pullwire takes. For a straight catheter, that length is equal to the articulating section, $L_o$. As the catheter bends (where a is the angle from the neutral axis, $r_c$, is the radius of the catheter, and T is the articulation angle), the path length is equal to $L_o-\cos(\alpha/90)*r_c*\tau$. The difference—$(\alpha/90)*r_c*\tau$—is the distance the pullwire must be actuated to make a catheter articulate to an angle τ, as illustrated in FIG. 3. From this concept, further solid mechanic and kinematic modeling is used via algorithms in the control computer to convert a desired catheter position or orientation as provided by the user into commands to the instrument driver to rotate motors designated for each pullwire.

Figure 4:
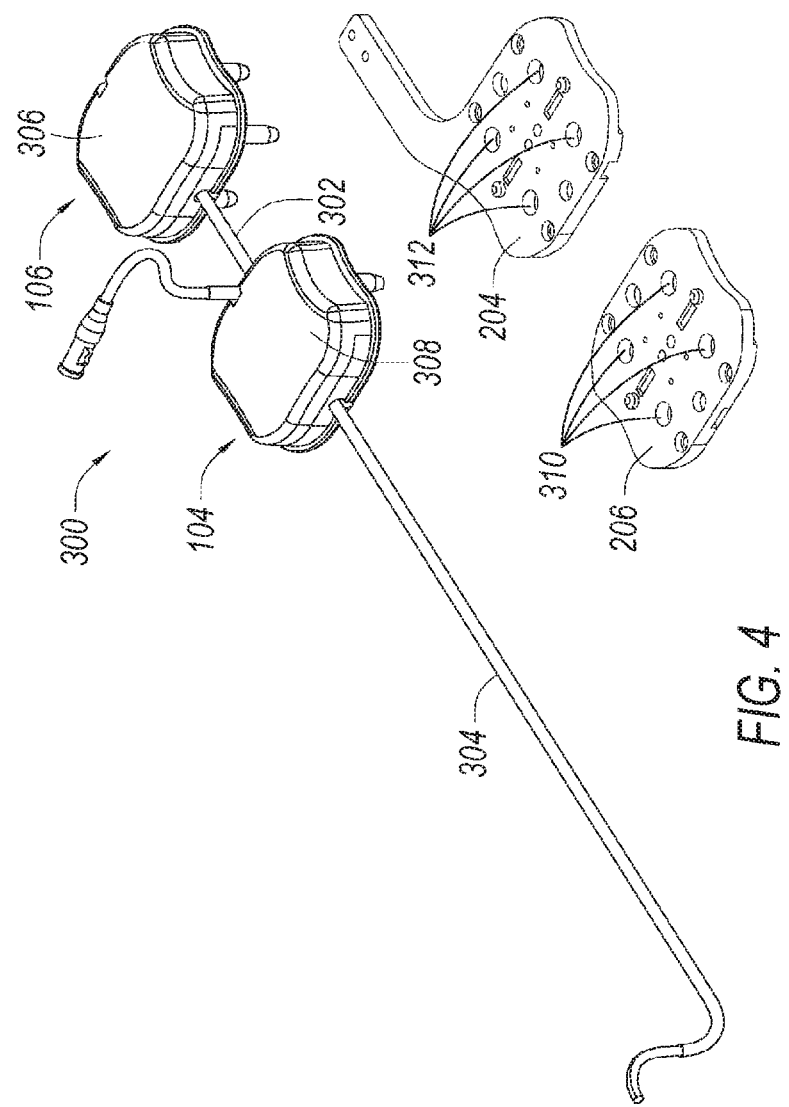
FIGS. 4 and 5 are partially exploded views of the catheter assembly of FIG. 2.
Figure 5:
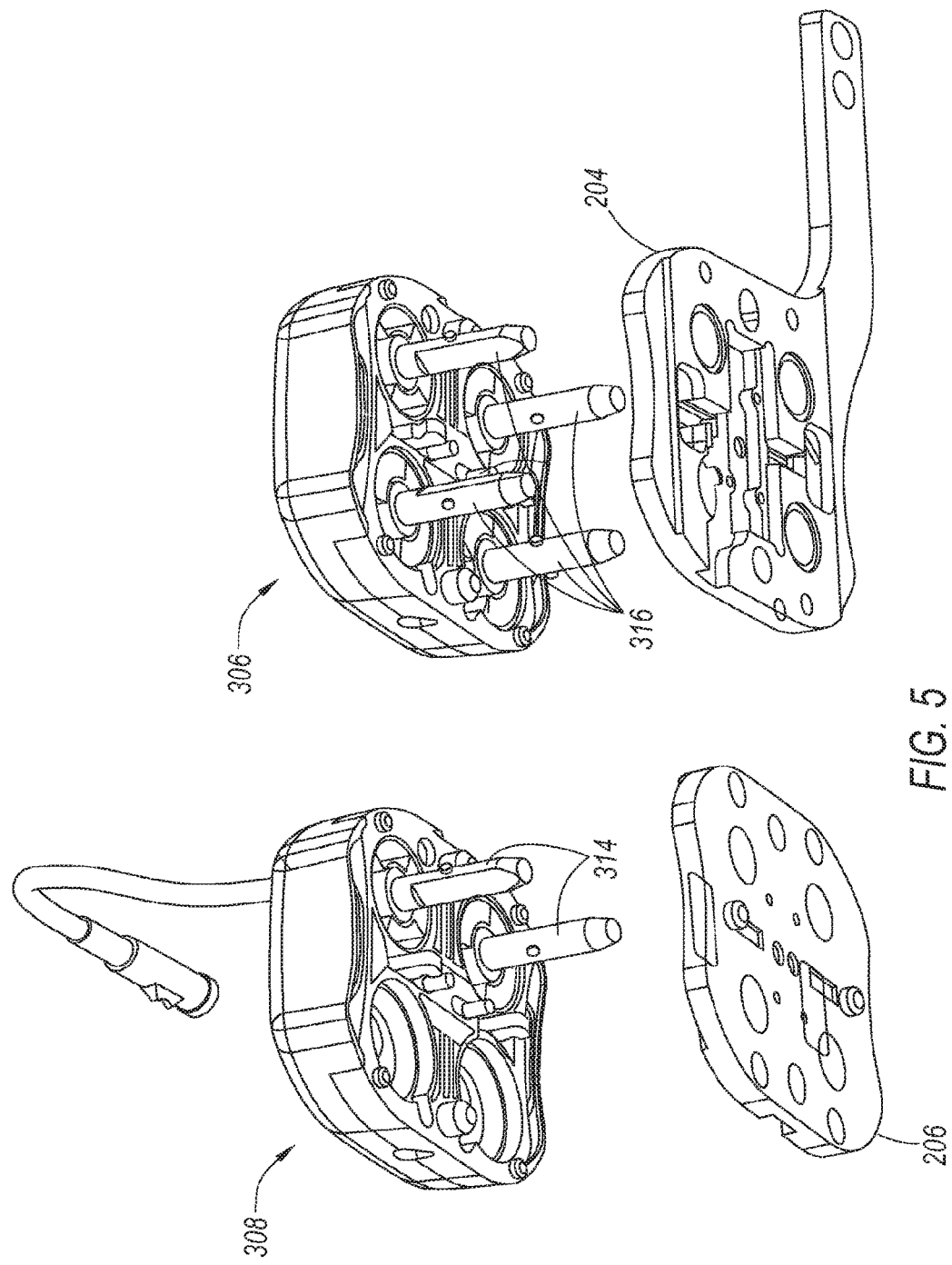

When a catheter is prepared for use with an instrument, its splayer is mounted onto its appropriate interface plate. In this case, as shown in FIG. 4, sheath splayer 308 is placed onto sheath interface plate 206 and a guide splayer 306 is placed onto guide interface plate 204. In the illustrated example, each interface plate 204, 206 has respectively four openings 310, 312 that are designed to receive corresponding drive shafts 314, 316 (FIG. 5 illustrates an underside perspective view of shafts 314, 316) attached to and extending from the pulley assemblies of the splayers 308, 306). Drive shafts 314, 316 are each coupled to a respective motor within instrument driver 108 (FIG. 2).

Figure 6:
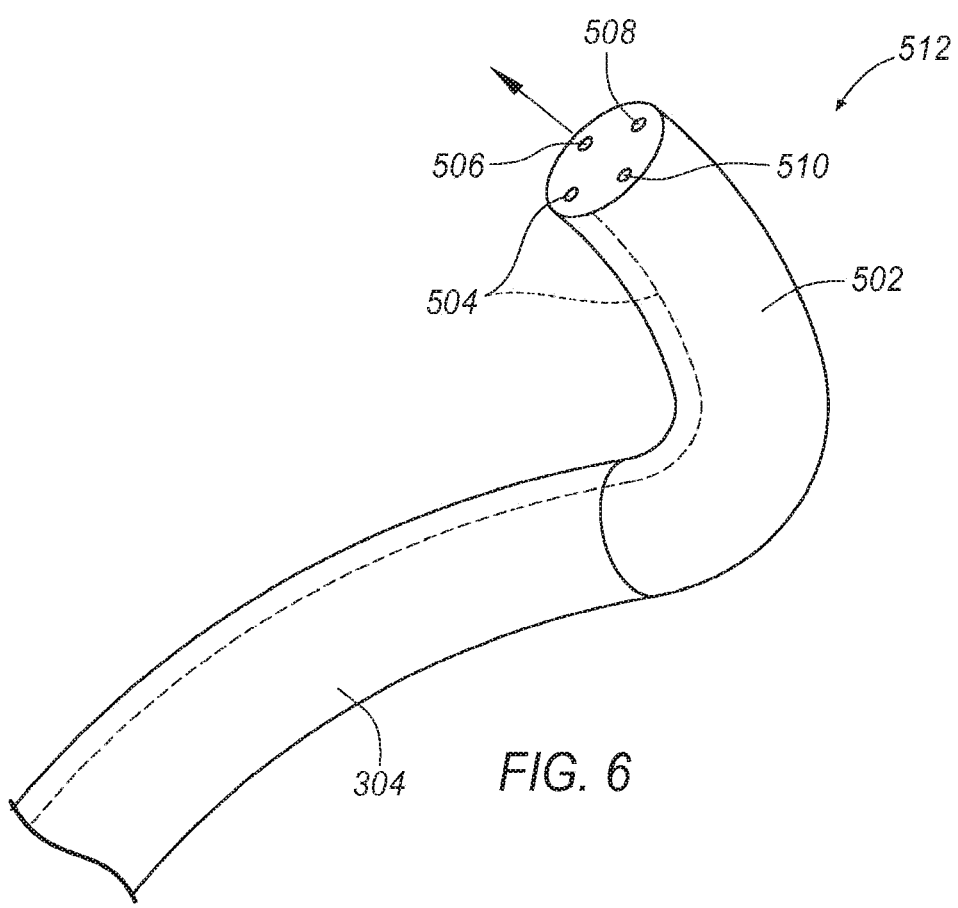
FIG. 6 illustrates an exemplary steerable catheter with pullwires.

Embodiments with less or more than four pullwires are contemplated by the present disclosure. When, e.g., a four-wire catheter 304 is coupled to instrument driver 108, each drive shaft 316 thereof is thereby coupled to a respective wire 504-510 (see FIG. 6). As such, a distal end 512 of catheter 304 can be articulated and steered by selectively tightening and loosening pullwires 504-510. Typically, the amount of loosening and tightening is slight, relative to the overall length of catheter 304. That is, each wire 504-510 typically need not be tightened or loosened more than perhaps a few centimeters. As such, the motors that tighten/loosen each wire typically do not rotate more than, for example, ¾ of a rotation. Thus, given the solid mechanics and kinematics of directing the instrument driver, a catheter (or other shapeable instrument) may be controlled in an open-loop manner, in which the shape configuration command comes into the beam mechanics and is translated to beam moments and forces, then translated into pullwire tensions as an intermediate value before finally translated into pullwire displacement given the entire deformed geometry. Based on the pullwire displacement command, a motor servo can apply the appropriate electrical current to produce the amount of rotation required to displace the pullwire.

Robotic systems use algorithms to determine the displacement of the pullwires to achieve the desired articulation of a catheter. However, differences between predicted and actual catheter position can result from the reliance by the kinematic model on certain assumptions and the lack of certain information. With rigid kinematics, simple geometry can be used to predict the location of any point along the rigid object given the following information: (1) a reference coordinate system; (2) an origin, or point in any coordinate system attached to the object; and (3) an orientation in any coordinate system attached to the object. Even with rigid structures, external forces, even gravity, may disrupt the ability to solve the location equation given the information above. If the above information is not sufficient to accurately describe the position of one point of an object from another point on the same object, then additional information must be provided, like the weight of the object, the forces acting on the object, the strength of the object, etc.

Standard equations and constants, like Poissons ratio, Hertzian stresses, Modulus of Elasticity, and linear stress/strain equations can improve on the kinematic model but these methods break down once the strains exceed the standard elastic range (usually about 3%). For example, a slim bar may be straight under no distal loading and the equations to predict the location of the distal end are fairly effective. However, when a load is placed on the beam, the distal end will deflect, or strain under the load. Even in a purely elastic response to the load, the location or orientation of the distal end of the beam is impossible to predict without knowing the magnitude, the direction, and the location of the external load. Similarly, flexible instruments such as catheters with low strength can be deflected by unknown loads at unknown locations and in unknown directions. Yet, prediction of the location and orientation of the distal end of a catheter is an important aspect of a robotic catheter system. The orientation of the distal end of the catheter based on information measured at the proximal end can better be determined through embodiments of the present disclosure.

The exemplary illustrations herein are directed to a variety of ideas for effectively measuring tension in catheter pullwires. Tension sensing could be used to enable or improve pretensioning, catheter control, slack wire management, catheter failure detection, etc., e.g., as discussed in U.S. patent application Ser. No. 13/828,342, which is incorporated by reference herein in its entirety. The specific concepts presented herein are directed to techniques for obtaining pullwire tension measurements and may be grouped into several categories: (1) measurement of torque in a drive train output shaft, (2) measurement of differential position across a compliant drive train, (3) measurement of reaction forces in a drive train mount, (4) measurement of torque in a secondary output shaft of a differential gearbox, and (5) measurement of side-load forces on an idler pulley in a splayer. Each will be addressed in further detail below.

Drivetrain System Overview

Figure 7:
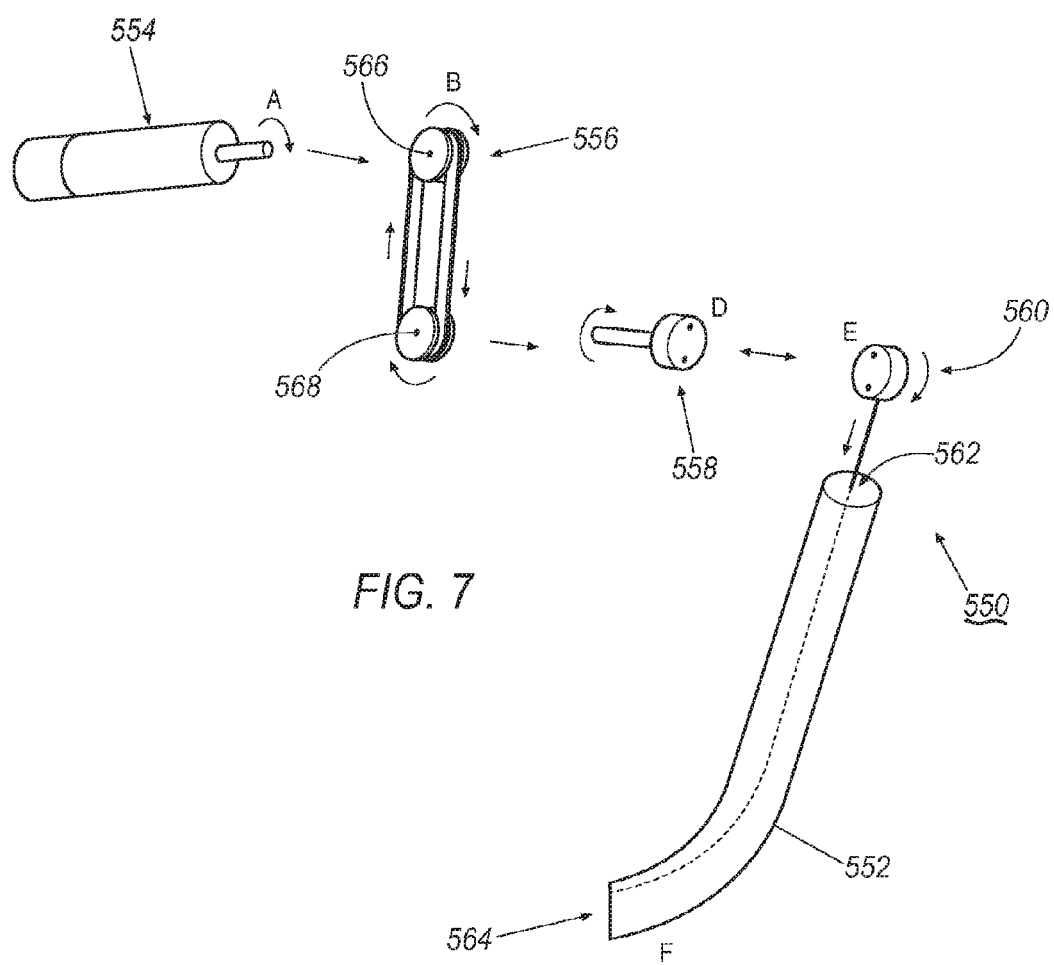
FIG. 7 is a schematic overview of catheter driveline components, according to one exemplary illustration.

Referring to FIG. 7, components of an exemplary drivetrain 550 for articulation of a catheter 552 are schematically illustrated. The drivetrain 550 components include a motor 554, a drivebelt/pulley/cable arrangement 556, an output shaft 558, a catheter pulley 560, and an articulation pull wire 562. The motor 554 ultimately controls a catheter tip 564 position. To this end, motor 554 drives the drive pulley 566. The drive pulley 556 drives a driven pulley 558, which in turn drives the output shaft 558. The output shaft 558 drives the catheter pulley 560, thereby articulating a pullwire 562, which in turn articulates the catheter tip 564.

Measurement of Torque in the Output Shaft of the Instrument Driver

In one exemplary arrangement, torque may be measured in the output shaft of an instrument driver. For example, torque may be measured in an output shaft of an instrument driver by mounting a strain gauge to the output shaft, e.g., to output shaft 558 of the drivetrain 550. Additionally, if a diameter of the catheter pulley 560 is known, the output shaft torque may be converted into a pullwire tension.

Turning now to FIGS. 8A-8D, another exemplary instrument driver 850 is illustrated. As with instrument driver 108 described above (FIG. 2), motors 854 within instrument driver 850 may be controlled such that carriages coupled to mounting plates 804, 806 are driven forwards and backwards on bearings. As a result, a catheter can be controllably manipulated while being inserted into the patient. The motors 854 may be activated to control bending of the catheter as well as the orientation of the distal tips thereof, including tools mounted at the distal tip.

The instrument driver 850 generally employs self-contained torque sensors 870 configured to measure torque of respective output shafts 858. Each of the torque sensors 870 may be incorporated in series with their respective output shaft 858. In this manner, tension sensing is accomplished with a direct torque measurement at the closest location to the catheter and articulation pulley as is possible, since the sensors 870 are mounted on the driveshaft 858. This direct torque measurement on the driveshaft 858 provides a closer correlation to articulation pull wire (not shown in FIGS. 8A-8D) force in the catheter since torque is measured on the component, which is interacting directly with the pullwire.

Figure 8B:
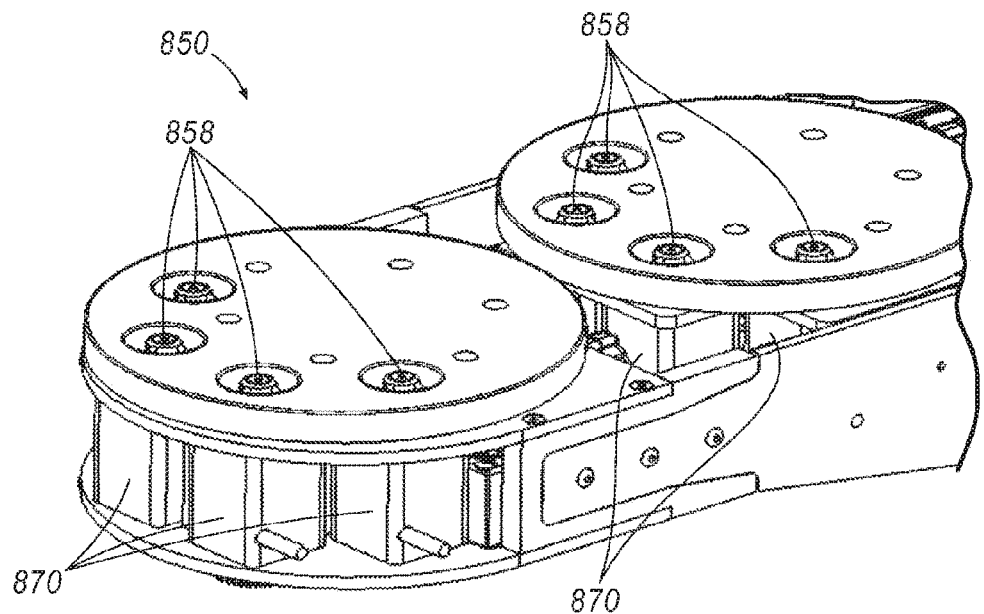
FIG. 8B is an enlarged perspective view of the exemplary instrument driver of FIG. 8A.
Figure 8C:
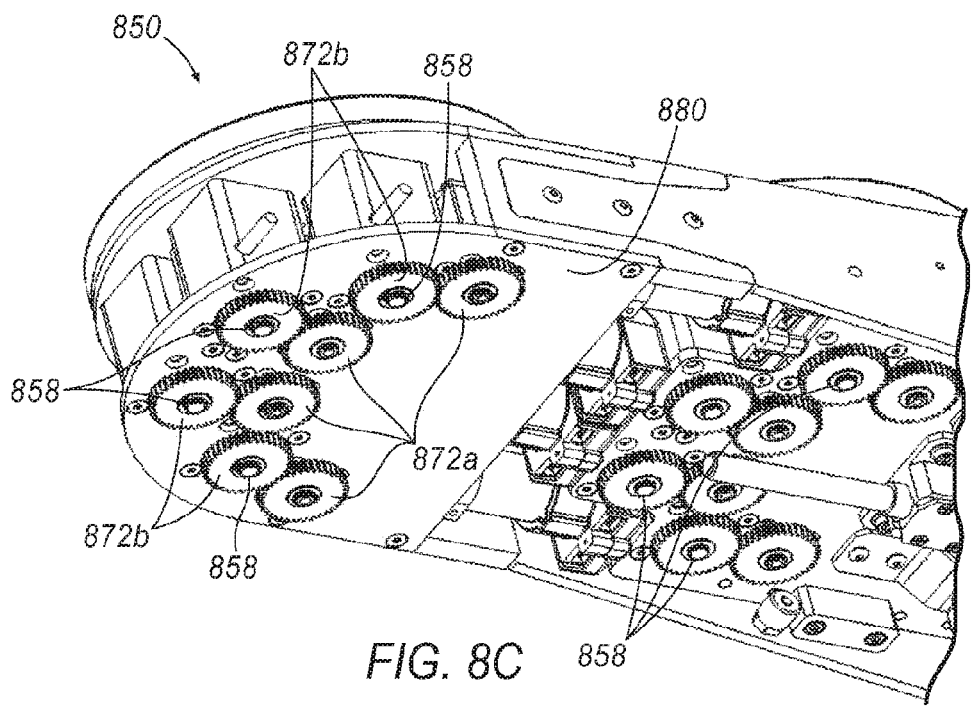
FIG. 8C is another perspective view of the exemplary instrument driver of FIGS. 8A and 8B.
Figure 8D:
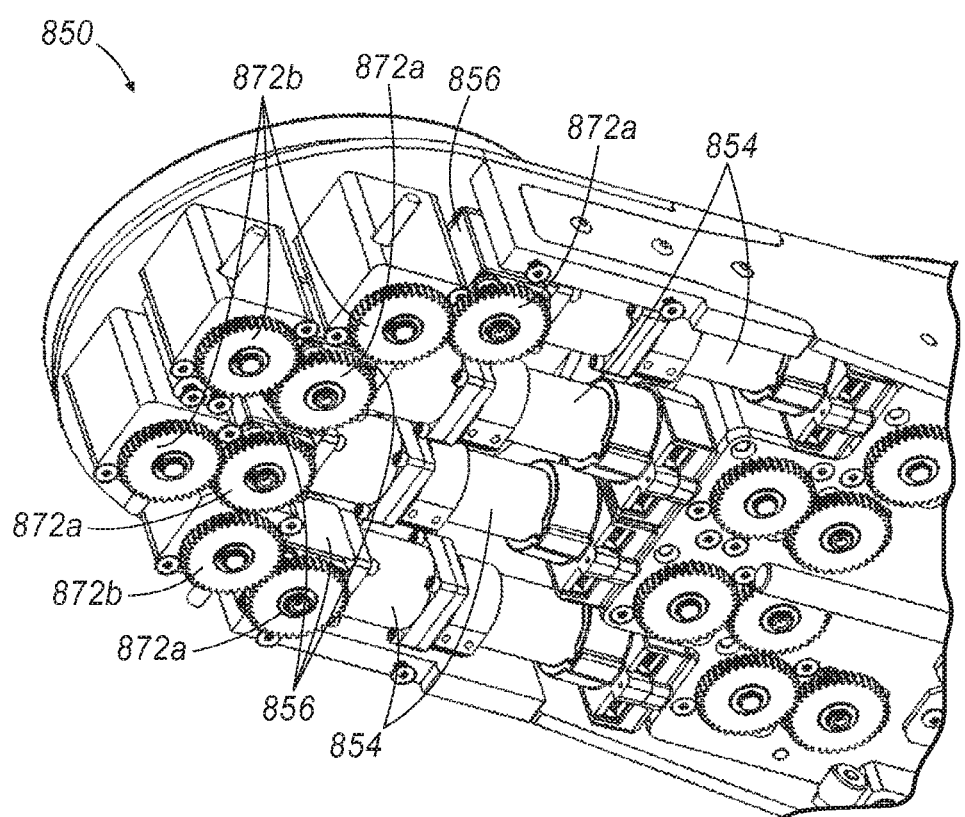
FIG. 8D is another perspective view of the exemplary instrument driver of FIGS. 8A-8C, with a cover panel removed.

As is shown in FIGS. 8A-8D, each axis has a drive mechanism. More specifically, as best seen in FIG. 8D, which illustrates an underside of the instrument drive 850 with a cover 880 (see FIG. 8C) removed, a plurality of motors 854 are provided, with a single motor for each axis. In one example, the motors 854 are a DC brushed motor. Motors 854 are each fed into respective gearbox mechanisms 856, e.g., via a planetary gearset or any other input mechanism that is convenient. The gearbox mechanisms 856 may each increase torque and decrease rotational speed that is output from its respective motor 854. The gearbox mechanisms 856 are coupled to its respective rotary torque sensor 870 via any power transmission device that is convenient. For example, as best seen in FIGS. 8C and 8D, a set of gears may be provided, including an output gear 872a which is engaged with an input gear 872b to the torque sensor 870. Alternatively, the rotary torque sensors 870 may be directly coupled to the gearbox mechanism 856 or motor 854. The rotary torque sensor 870 may be attached directly to the output shaft 858. The output shaft 858 may drive the pull wires directly, or may in turn drive an articulation pulley (not shown in FIGS. 8A-8D), which drives the pull wires.

In one exemplary illustration, an exemplary rotary torque sensor 870 does not limit a range of motion of the output shaft 858, and measures torque output from the output shaft 858 directly as it rotates. Since the sensor 870 itself allows for infinite rotation, the system is not limited in its range of motion or degrees of freedom. Moreover, this arrangement is relatively simple as it allows mounting of the sensors 870 directly inline with the output shafts 858. Additionally, the inline mounting of the torque sensors 870 with the output shafts 858 reduces or may even eliminate calibration prior to measuring torque of the output shafts. The rotary torque sensor 870 may be a contactless or slip-ring type sensor employing a strain-gauge type torque measurement device, merely as examples.

Measurement of Differential Positions Across a Compliant Drive Train

Drivetrain position may be determined with optical encoders mounted directly to the motor shafts by assuming that the drivetrain is a rigid coupling between the motor position and the position of the output shafts of the instrument driver. However, in reality, the drivetrain is not perfectly rigid. Indeed, the drivetrain deflects to some degree under load. Thus, by placing a second measurement sensing device (such as, but not limited to, an optical encoder, magnetic encoder, potentiometer, etc.) on the output shaft of the instrument driver, the deflection of the drivetrain under load could be measured as a difference between the motor and output shaft positions. Given a known or assumed stiffness of the drivetrain, this measured deflection of the drivetrain will provide an estimate of the load in the drive train and therefore the tension in the pullwire.

To further increase the sensitivity of this pullwire tension estimate, compliance of the drivetrain could be intentionally increased, therefore increasing the amount of deflection available to be measured by the dual position measurements. In one exemplary configuration, the additional compliance may be provided in the form of linear springs in series with a cable-drive type drive train. In another exemplary arrangement, the additional compliance may be in the form of rotational springs in series with the output shaft itself.

A further option would be to encapsulate the additional compliance within some sort of floating cage or otherwise limit its deflection to some known maximum amount. While this technique would limit the largest pullwire tension that could be measured, this limited maximum deflection could be useful in calibration and improving fault tolerance.

Measurement of Reaction Forces in Drivetrain Mount

Another technique includes using measurement of reaction forces in a drivetrain mount to sense catheter tension. Various examples of this technique will be described.

Figure 9:
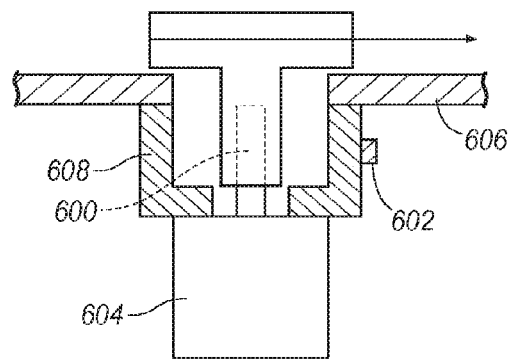
FIG. 9 illustrates an exemplary sensor mounting arrangement configured to measure output shaft torque for a catheter driveline.

As an alternative to measuring the torque in the output shaft directly, measurement of the reaction forces from the entire geartrain may be measured. As shown in FIG. 9, if the motor 604 (with optional gearbox) is mounted to a chassis of the instrument driver 606 through a sensed mounting structure 608, then at static equilibrium the measured reaction torque is equal to the output shaft 600 torque. The sensed mounting structure 608 could be a self-contained torque sensor, a hinge, or flexure-based structure with integrated load cells or strain gauges, or a strain gauge 602 mounted to an otherwise rigid mounting structure.

One difficulty that may be experienced with this technique, i.e., where the motor 604 is oriented parallel to the output shaft 600, is that in addition to the output shaft torque, the sensor 602 would also pick up inertial forces from the acceleration and deceleration of the motor 604. Options for minimizing this contamination include: low-pass filtering the measured signal, only using data collected when the motor 604 was stationary or moving at a roughly constant velocity, modeling the inertial effects of the motor 604 and compensating the measured signal based upon a measured acceleration from the motor encoder and/or motor back-Electromotive Force (EMF).

Figure 10:
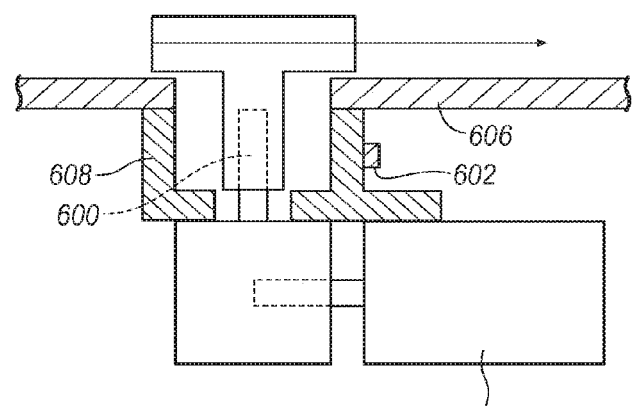
FIG. 10 illustrates a sensor mounting arrangement configured to measure output shaft torque for an alternative catheter driveline configuration.

In another exemplary arrangement, referring to FIG. 10, by mounting the axis of the motor 604 at ninety degrees to the axis of the output shaft 600, the inertia forces due to accelerating and decelerating the motor 604 will be decoupled from the measured reaction torque. The acceleration of the output shaft 600, pulley, etc. still can contaminate the measurement of pullwire tension, but these contributions will be quite small compared the acceleration of the motor rotor, especially because of the effects of gear reduction between motor 604 and output shaft 600. Similar to the axial configuration above, the sensed mounting structure 608 could be a self-contained torque sensor, a hinge or flexure based structure with integrated load cells or strain gauges, or a strain gauge 602 mounted to an otherwise rigid mounting structure.

One of the challenges with measuring the torque in the output shaft directly is that the output shaft 600 must be free to rotate, potentially numerous complete revolutions. This requirement can make routing the necessary signal connections (electrical, fiber optic, etc.) to the sensing element challenging.

Figure 11:
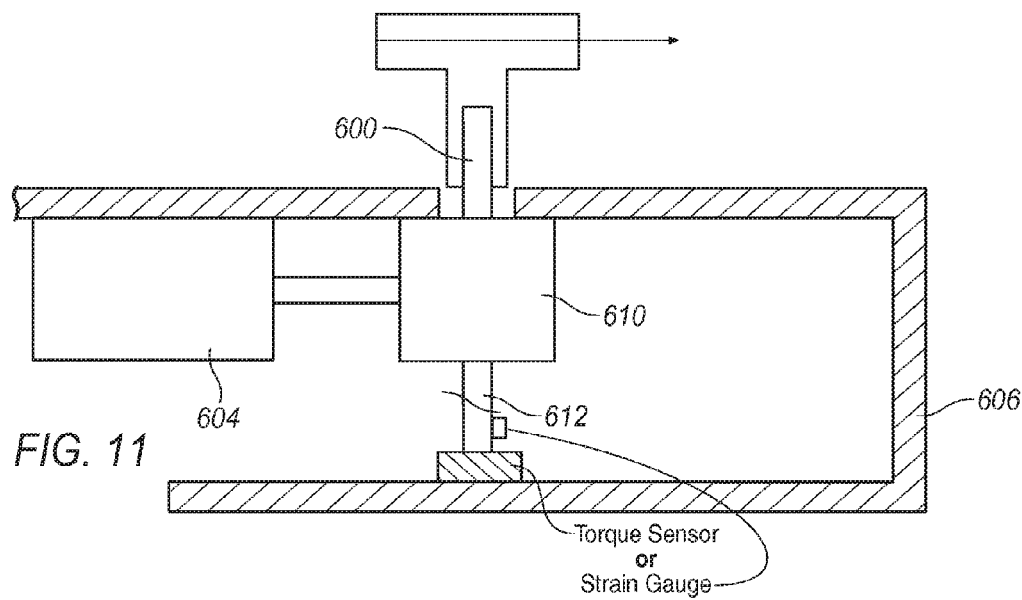
FIG. 11 illustrates a sensor mounting arrangement configured to measure output shaft torque for an alternative catheter driveline configuration.

Turning now to FIG. 11, another example is illustrated where torque is measured in a secondary output shaft of a differential gearbox. Measuring torque in a secondary output shaft may address the challenges of signal connection routing by placing the sensing element (a self-contained torque sensor or a strain gauge instrumented shaft or flexure) in a part of the drivetrain that does not rotate but still shares the same torque as the output 600. More specifically, this may be accomplished by use of a differential gearbox 610 similar to that used in transferring power to both wheels of an automobile while allowing them to rotate at different speeds. One of the output shafts 600 of the differential gearbox 610 is used to drive the catheter pulley while the other output shaft 612 is fixed to ground (i.e., the chassis of the instrument driver 606) through some sort of torque sensing element. Theoretically, the only difference between the torque in the upper and lower output shafts 600, 612 is due to inefficiencies of the differential gearbox 610. By focusing on maximizing the efficiency of the differential gearbox 610, this configuration may generally provide a good estimate of the pullwire tension without having to address the challenges of routing signal connections to a sensor that is moving.

In another exemplary approach similar to that shown in FIG. 11, the secondary (fixed) output shaft and the sensing element are incorporated entirely within the housing of the differential gearbox itself Such an arrangement may provide for a more compact gearbox with integrated output shaft torque sensing and no limitations on output shaft motion.

Measurement of Side-load Forces on Idler Pulley in a Splayer

All of the above described concepts for sensing catheter tension rely in one way or another on sensing or estimating the torque in the output shaft of the instrument driver and then converting the sensed torque into a pullwire tension estimate based upon the radius of the catheter pulley, while assuming that no other disturbance forces are acting upon the catheter pulley.

Figure 12A:
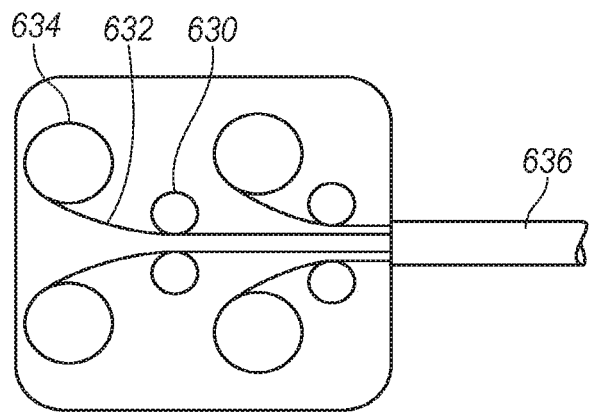
FIG. 12A illustrates a mounting configuration for pullwires in a splayer, according to one exemplary illustration.
Figure 12B:
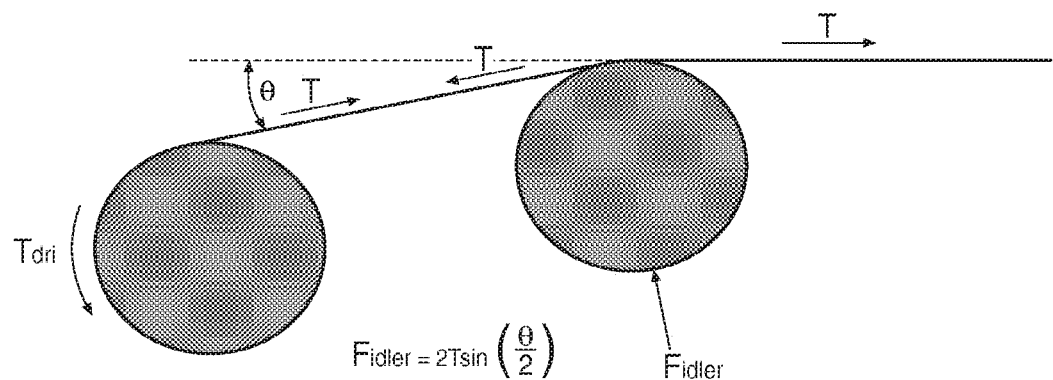
FIG. 12B is an illustration of the side-load force on an idler pulley, e.g., consistent with the illustration of FIG. 12A.

In another exemplary approach illustrated in FIGS. 12A and 12B, an idler pulley 630 may be placed slightly in the path of the pullwire 632 between the drive pulley 634 and the catheter body 636 and measure the resulting side-load on the idler pulley. This technique has the advantage of more directly measuring the tension on the pullwire 632 itself and is not affected by friction and other inefficiencies in the drivetrain. Additionally, because side-load is being measured rather than torque in the idler pulley, the pulley can be free to spin (in a bearing for example) and the sensing element does not have to move as the pullwires 632 are actuated.

As illustrated in FIG. 12B, the side-load force on the idler pulley (F-idler) is directly related to the tension in the pullwire. Side-load force on the idler pulley may be measured, merely as examples, by using a force sensing element located in a splayer, or by using a force sensing element located in an instrument driver. Each will be discussed in turn.

The most direct way to measure the side-load force on the idler pulley (and therefore the pullwire tension) may be to measure the side load force on the idler pulley at the mounting of the idler pulley in the splayer itself, e.g., with a strain gauge or load cell.

Figure 13:
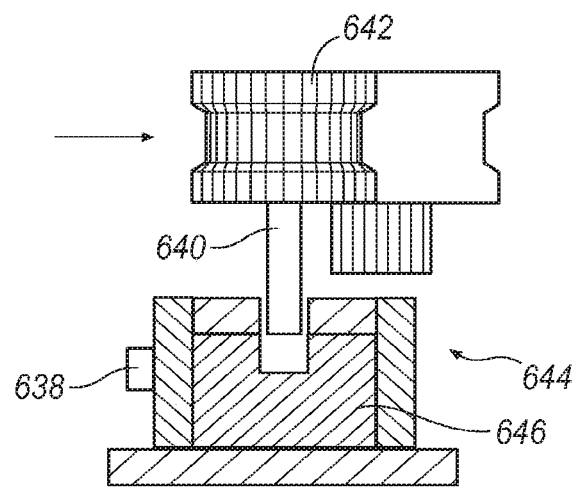
FIG. 13 illustrates a sensor mounting arrangement for an instrument driver.

While implementing a force sensing element in a splayer provides a direct measurement, it may generally increase the cost associated with disposable elements of the system. Thus, referring to FIG. 13, to minimize such costs, the force sensing element 638 may be relocated into the instrument driver itself, which is a non-disposable component, by extending the shaft 640 of the idler pulley 642 down through a sterile barrier into the instrument driver along with the shaft of the drive pulley. As the idler pulley 642 is preferably be free to rotate, its shaft may be supported by a bearing assembly 644. This bearing assembly 644 would then in turn be grounded to the chassis of the instrument driver through an instrumented mounting structure 646. This instrumented mounting structure 646 could be a hinge or flexure based mount incorporating a load cell or strain gauge. It may also be constructed to either measure the linear side load on the idler pulley 642 or the resulting moment caused by the side-load acting at a known distance above the mounting structure.

Figure 14A:
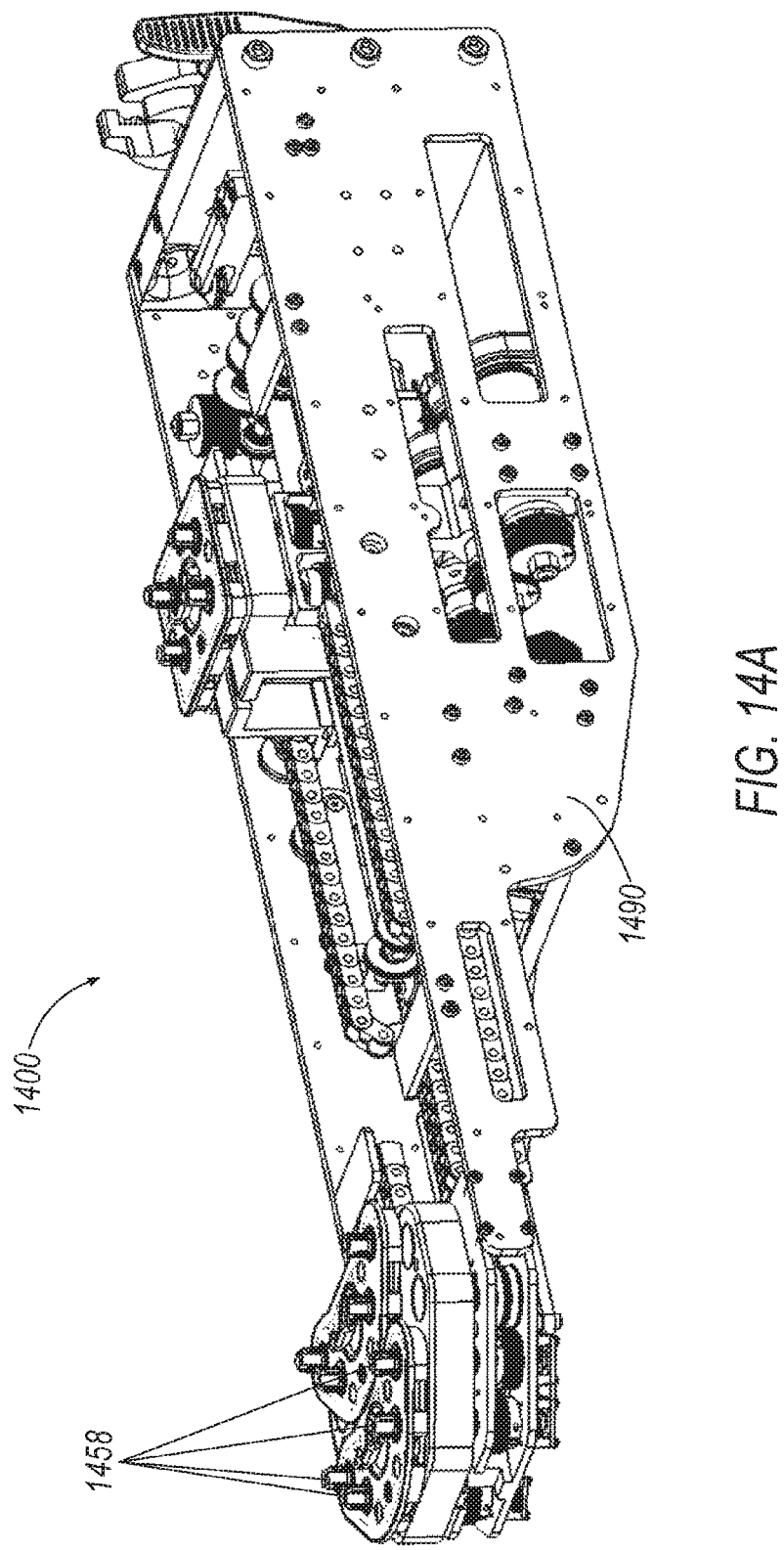
FIG. 14A is a perspective view of another exemplary instrument driver for a catheter assembly, which employs a sensor mounting arrangement for an instrument driver.
Figure 14B:
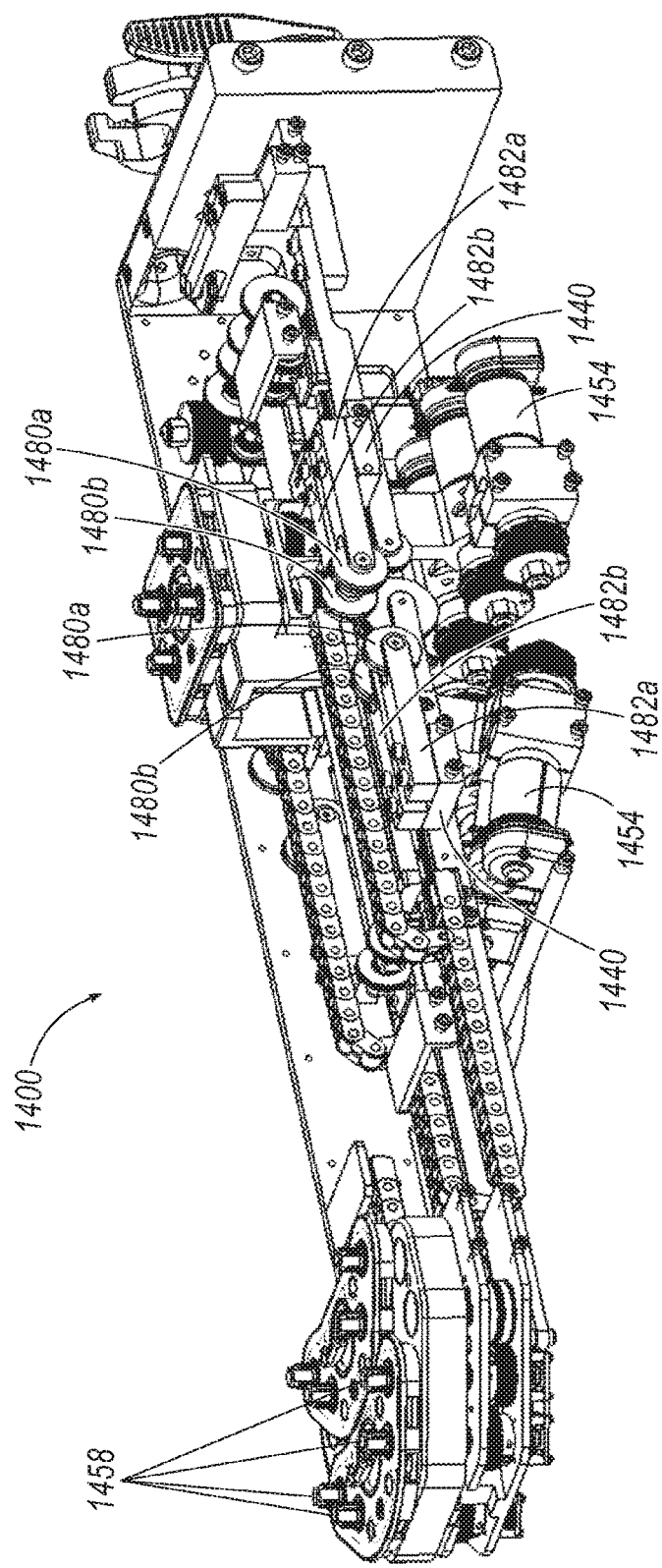
FIG. 14B is a perspective view of the exemplary instrument driver of FIG. 14A, with a side panel removed.
Figure 14C:
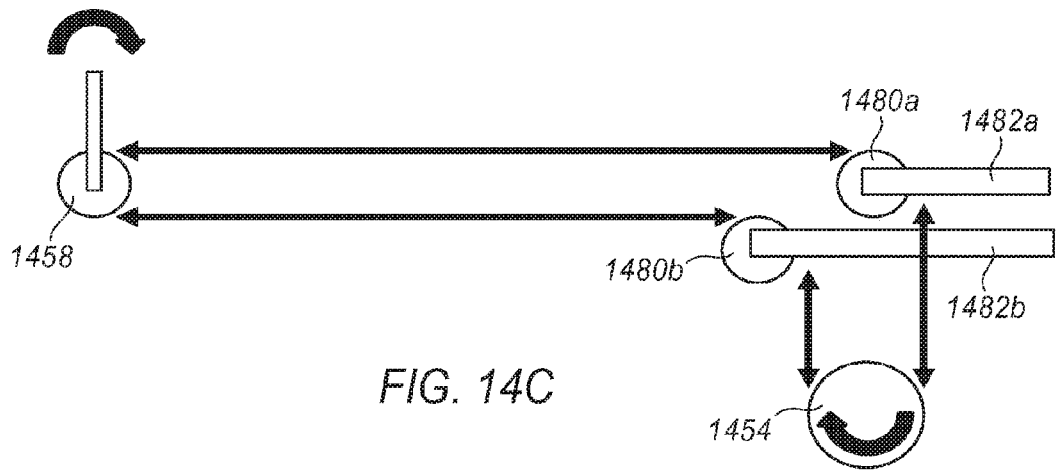
FIG. 14C is a schematic illustration of components of the instrument driver shown in FIGS. 14A and 14B, according to an exemplary illustration.

Turning now to FIGS. 14A-14C, another exemplary illustration of a force sensing element incorporated into a splayer to provide a direct measurement is illustrated. The instrument driver 1400 includes a plurality of motors 1454 for each axis of a catheter (not shown in FIGS. 14A-14C). The motors 1454 are each linked to respective output shafts 1458, which in turn may actuate a pullwire (not shown in FIGS. 14A-14C) of the catheter.

As best seen in FIG. 14B, which illustrates the instrument driver 1400 without a side panel 1490 (see FIG. 14A), and also FIG. 14C, which illustrates components of the instrument driver 1400 schematically, the motors 1454 of the instrument driver 1400 may each rotate to actuate output shaft 1458 by way of a pair of pulleys 1480a, 1480b. The pulleys 1480a, 1480b are mounted on respective load beams 1482a, 1482b. The load beams 1482a, 1482b are each cantilever mounted within the instrument driver 1400, e.g., to a support block 1440. In this manner, when a motor 1454 rotates to actuate a pullwire by rotating its respective output shaft 1458, the load beams 1482a, 1482b will deflect in response. The deflection of the load beams 1482a, 1482b correlates to torque at the output shaft 1458.

Figure 15:
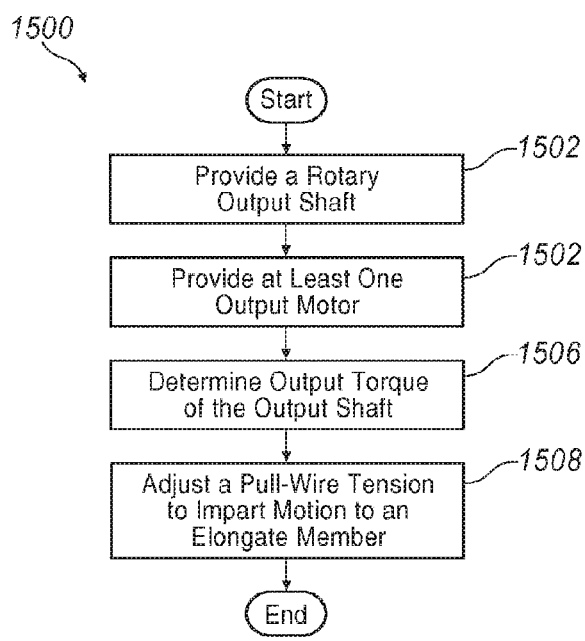
FIG. 15 is a process flow diagram for an exemplary method of measuring an output torque.

Turning now to FIG. 15, an exemplary process 1500 is illustrated for determining an output torque. Process 1500 may begin at block 1502, where a rotary output shaft is provided. For example, exemplary rotary output shafts are described above for actuating an elongate member, e.g., by way of one or more pull wires.

Proceeding to block 1504, at least one output motor may be provided. For example, as described above, exemplary output motors may be configured to actuate movement of the elongate member by rotating the output shaft. Process 1500 may then proceed to block 1506.

At block 1506, an output torque of the output shaft may be determined, e.g., based at least upon one sensor input. For example, a rotary torque sensor input may be used, in which the rotary torque is measured via a direct contact with the output shaft. In other exemplary approaches, a load beam or load cell may be employed. In examples where a load cell is employed, the load cell may be configured to measure the output shaft torque based upon at least a deflection of the load cell. More specifically, exemplary load cells may be used having a cantilever mounting within the instrument driver.

Proceeding to block 1508, a pullwire tension may be adjusted, e.g., to impart motion to a tip of the elongate member. For example, as noted above exemplary output shafts may be employed to actuate one or more pull wires of an elongate member, e.g., a catheter.

The exemplary systems and components described herein, e.g., workstation 112, electronics rack 118, the exemplary instrument drivers, and/or any components thereof, may include a computer or a computer readable storage medium implementing the operation of drive and implementing the various methods and processes described herein. In general, computing systems and/or devices, such as user input devices included in the workstation 112 or any components thereof, merely as examples, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many examples and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A robotic surgical system, comprising:
an elongate member comprising a pull wire disposed therein;
an input device configured to receive a user input;
an instrument driver operatively coupled to the elongate member, the instrument driver comprising a motor and a rotary torque sensor configured to generate torque data indicative of a torque imparted on the pull wire; and
a control system operatively coupled to the input device and the instrument driver, wherein the elongate member is controllable by the instrument driver based on a command generated by the control system in response to the user input and the torque data.

2. The robotic surgical system of claim 1, wherein the motor comprises a rotary output motor.

3. The robotic surgical system of claim 1, wherein the motor comprises a servo motor.

4. The robotic surgical system of claim 1, wherein the motor comprises a DC brushed motor.

5. The robotic surgical system of claim 4, wherein the rotary torque sensor measures an output shaft torque via a direct contact with the output shaft.

6. The robotic surgical system of claim 4, wherein the rotary torque sensor is positioned in series with the output shaft.

7. The robotic surgical system of claim 1, wherein the instrument driver further comprises an output shaft coupled to the motor and the rotary torque sensor.

8. The robotic surgical system of claim 1, wherein the pull wire is operatively coupled to the output shaft such that rotation of the output shaft results in displacement of the pull wire.

9. The robotic surgical system of claim 8, wherein the command generated by the control system is configured to actuate the motor to thereby drive the output shaft, adjust tension in the pull wire, and impart motion to an articulation section of the elongate member.

10. The robotic surgical system of claim 8, wherein the torque imparted on the pull wire is imparted by the output shaft.

11. The robotic surgical system of claim 1, wherein the instrument driver further comprises a gearbox coupled to the motor.

12. The robotic surgical system of claim 11, wherein the gearbox comprises a planetary gearset or a differential gearbox.

13. The robotic surgical system of claim 11, wherein the gearbox is configured to increase a torque and decrease a rotational speed output from the motor.

14. The robotic surgical system of claim 11, wherein the rotary torque sensor is directly coupled to the gearbox.

15. The robotic surgical system of claim 11, wherein the rotary torque sensor is coupled to the gearbox via a power transmission device.

16. The robotic surgical system of claim 11, wherein the rotary torque sensor is positioned to measure torque in a secondary output shaft of the gearbox.

17. The robotic surgical system of claim 1, wherein the rotary torque sensor is directly coupled to the motor.

18. The robotic surgical system of claim 1, wherein the rotary torque sensor comprises a contactless or slip-ring type sensor.

19. A robotic surgical system, comprising:
an elongate member;
an input device configured to receive a user input;
an instrument driver operatively coupled to the elongate member, the instrument driver comprising a motor and a rotary torque sensor configured to generate torque data; and
a control system operatively coupled to the input device and the instrument driver, wherein the elongate member is controllable by the instrument driver based on a command generated by the control system in response to the user input and the torque data, wherein the instrument driver further comprises one or more additional motors and one or more additional rotary torque sensors, wherein each of the one or more additional motors is coupled to a different one of the one or more additional rotary torque sensors.

20. The robotic surgical system of claim 19, wherein the elongate member comprises a plurality of pull wires, and wherein each of the motor and the one or more additional motors is configured to actuate a different one of the plurality of pull wires.

* * * * *